(12) United States Patent
Adamczyk et al.

(10) Patent No.: US 7,811,749 B2
(45) Date of Patent: Oct. 12, 2010

(54) MEASURING FREE CHOLINE TO DETERMINE SUITABILITY OF ERYTHROCYTES FOR TRANSFUSION

(75) Inventors: Maciej Adamczyk, Gurnee, IL (US); Roy Jeffrey Brashear, Mundelein, IL (US); Phillip G. Mattingly, Third Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 226 days.

(21) Appl. No.: 12/106,670

(22) Filed: Apr. 21, 2008

(65) Prior Publication Data

US 2009/0263845 A1 Oct. 22, 2009

(51) Int. Cl.
*A01N 1/02* (2006.01)
(52) U.S. Cl. .......................................... 435/2; 435/7.25
(58) Field of Classification Search .................... 435/2, 435/7.25
See application file for complete search history.

(56) References Cited

U.S. PATENT DOCUMENTS

| | | |
|---|---|---|
| 5,241,070 A | 8/1993 | Law et al. |
| 5,468,646 A | 11/1995 | Mattingly et al. |
| 5,543,524 A | 8/1996 | Mattingly et al. |
| 5,783,699 A | 7/1998 | Mattingly et al. |
| 6,210,976 B1 | 4/2001 | Sabbadini |
| 6,830,932 B1 | 12/2004 | Danne et al. |

OTHER PUBLICATIONS

Tinmouth A. et al. Clinical Consequences of Red Cell Storage in the Critically Ill. Transfusion 46(11)2014-2027, Nov. 2006.*
Abernethy, etal., "An enzymatic Method for Erythrocyte Acetylcholinesterase," Clin. Chem., 34:6 (1998), pp. 1055-1057.
Adamczyk, etal., "Chemiluminescent N-Sulfonylacridinium-9-Carboxamides and Their Application in Clinical Assays," Dyke Ed., CRC Press LLC, (2002): Boca Raton, pp. 77-105.
Adamczyk, etal., "Choline Concentration in Normal Blood Donor and Cardiac Troponin-Positive Plasma Samples," Clin Chem, 52 (2006), pp. 2123-2124.
Adamczyk, etal., "Elevation of choline concentration in cardiac troponin-I positive human plasma," In Proceedings of the 14th International Symposium on Bioluminescence and Chemiluminescence. Chemistry, Biology and Applications (A. A. Szalay, P.J. Hill, L.J. Kricka and P.E. Stanley, Eds.), pp. 59-62, World Scientific, Hackensack, NJ, (© 2007).
Adamczyk, etal., "High Throughput Detection of Hydrogen Peroxide. Validation of Homogeneous Chemiluminescent Assays for Choline on Human Plasma and Whole Blood," In Proceedings of the 14th International Symposium on Bioluminescence and Chemiluminescence. Chemistry, Biology and Applications (A.A. Szalay, P.J. Hill, L.J. Kricka and P.E. Stanley, Eds.) (2007), pp. 63-66, World Scientific, Hackensack, NJ.
Adamczyk, etal., "Homogeneous chemiluminescent assays for free choline in human plasma and whole blood," Analytica Chimica Acta, 579 (2006), pp. 61-67.
Adamczyk, etal., "Linker-Mediated Modulation of the chemiluminescent Signal from N(subscript 10)-(3-Sulfopropyl)-N-sulfonylacridinium-9-carboxamide Tracers," Bioconjugate Chem., 11, (2000), pp. 714-724.
Adamczyk, etal., Modulation of the Chemiluminescent Signal from $N^{10}$-(3-Sulfopropyl)-*N*-Sulfonylacridinium-9-carboxamides, Tetrahedron 55 (1999), pp. 10899-10914.
Adamczyk, etal., "Rapid high-throughput detection of peroxide with an acridinium-9-carboxamide: A homogeneous chemiluminescent assay for plasma choline," Bioorg. Med. Chem. Lett., 16 (2006), pp. 2407-2410.
Adamczyk, etal., "Regiodependent Luminescence Quenching of Biotinylated N-Sulfonyl-acridinium-9-carboxamides by Avidin," Organic Letters, 5:21 (2003), pp. 3779-3782.
Adamczyk, etal., "Synthesis of a Chemiluminescent Acridinium Hydroxylamine (AHA) for the Direct Detection of Abasic Sites in DNA," Organic Letters, 1:5, (1999), pp. 779-781.
Adamson., "New Blood, Old Blood, or No Blood?," New England Journal of Medicine, 358:12 (2008), pp. 1295-1296.
Beilharz, etal., "Determination of choline in erythrocytes using high-resolution proton nuclear magnetic resonance spectroscopy: comparison with a choline oxidase method," Anal. Biochem., 137 (1984), pp. 324-329.
Biagini, etal., "Characterization of the choline carrier of *Plasmodium falciparum*: a route for the selective delivery of novel antimalarial drugs," Blood, 104 (2004), pp. 3372-3377.
Carvalho, etal., "Acetylcholine and Choline Effects on Erythrocyte Nitrite and Nitrate Levels," Journal of Applied Toxicology, 24 (2004), pp. 419-427.
Cornford, etal., "Carrier Mediated Blood-Brain Barrier Transport of Choline and Certain Choline Analogs," Journal of Neurochemistry, 30 (1978), pp. 299-308.
Damsma, etal., "Liquid chromatography with electrochemical detection for the determination of choline and acetylcholine in plasma and red blood cells. Failure to detect acetylcholine in blood of humans and mice," J. Chromatogr., 428 (1988), pp. 1-8.
Danne, etal., "Prognostic implications of elevated whole blood choline levels in acute coronary syndromes," Am. J. Cardiol., 91, (2003), pp. 1060-1067.
Danne, etal., Spectrum of Whole Blood Choline concentrations in Critically Ill Patients Measured with High-Performance Liquid Chromatography Electrospray Ionization Mass Spectrometry, XIX International Congress of Clinical chemistry, IFCC/AACC 2005 Annual Meeting Jul. 24-28, 2005, Orlando, Florida, Abs. No. A-77.

(Continued)

*Primary Examiner*—Ralph Gitomer
(74) *Attorney, Agent, or Firm*—Carol Larcher, Larcher & Chao Law Group; Audrey L. Bartnicki

(57) ABSTRACT

A method of assessing whether or not erythrocytes are suitable for transfusion into a recipient comprising (i) assaying a sample of erythrocytes for free choline, and (ii) comparing the level of free choline in the sample with the level of free choline deemed suitable for transfusion therapies; and a kit for use in such a method comprising at least one reagent for assaying the sample, instructions for conducting the assaying of the sample, and guidelines for assessing the suitability of the erythrocytes for transfusion.

3 Claims, 3 Drawing Sheets

OTHER PUBLICATIONS

Danne, etal., "Whole blood choline and plasma choline in acute coronary syndromes: prognostic and pathophysiological implications," Clin Chim Acta 383 (2007), pp. 103-109.

Danne, etal., "Whole-blood hypercholinemia and coronary instability and thrombosis," Clin Chem 51 (2005), pp. 1315-1317.

Danne, etal., "Whole Blood Choline and Plasma Choline Concentration for Early Risk-Stratification of Troponin I-Negative Acute Coronary Syndromes," The American Heart Association Scientific Sessions, Nov. 9-12, Orlando, Florida, Abs. No. AOP.46.1/2150, (2003).

Das, etal., "Determination of Free Choline in Plasma and Erythrocyte Samples and Choline Derived from Membrane Phosphatidylcholine by a Chemiluminescence Method," Analytical Biochemistry, 152 (1986), pp. 178-182.

Deves, etal., "The Comparative Specificity of the Inner and Outer Substrate Transfer Sites in the Choline Carrier of Human Erythrocytes," The Journal of Membrane Biology, 80 (1984), pp. 71-80.

Deves, etal., "The binding and translocation steps in transport as related to substrate structure. A study of the choline carrier of erythrocytes," Biochim Biophys Acta, 557 (1979), pp. 469-485.

Deves, etal., "Evidence for a Two-State Mobile Carrier Mechanism in Erythrocyte Choline Transport: Effects of Substrate Analogs on Inactivation of the Carrier by N-Ethylmaleimide," The Journal of Membrane Biology, 61 (1981), pp. 21-30.

Fuchs, etal., "The phosphatidylcholine/lysophosphatidylcholine ration in human plasma is an indicator of the severity of rheumatoid arthritis: Investigations by $^{31}$P NMR and MALDI-TOF MS," Clinical Biochemistry, 38 (2005) pp. 925-933.

Hardman, etal., "Characterization of the Erythrocyte Sodium-Lithium Countertransporter: Limitations and Assumptions of Traditional and Kinetic Methodologies," The Journal of Membrane Biology, 161 (1998), pp. 197-205.

Henderson, etal., "The action of certain antibiotics on mitochondrial, erythrocyte and artificial phospholipids membranes," Biochem J, 111 (1969), pp. 521-535.

Jones, etal., "Measurement of choline concentration and transport in human erythrocytes by 1H NMR: comparison of normal blood and that from lithium-treated psychiatric patients," Clin. Chim. Acta, 104 (1980), pp. 77-85.

Jope, etal., "Choline flux in human erythrocytes," Psychopharmacol. Bull., 20 (1984), pp. 674-680.

Klein, etal., "Transfusion Medicine 1, Red blood cell transfusion in clinical practice," Lancet, 370 (2007), pp. 415-426.

Klein, etal., "The Transfusion of red cells", Mollison's Blood Transfusion in Clinical Medicine, 11th Ed., (2006), Blackwell Publishing Ltd., pp. 352-405.

Koch, etal., "Duration of Red-Cell Storage and Complications after Cardiac Surgery," The New England Journal of Medicine, 358:12, (2008), pp. 1229-1239.

Krupka, etal., "The Choline Carrier of Crythrocytes: Location of the NEM-Reactive Thiol Group in the Inner Gated Channel,"The Journal of Membrane Biology, 101 (1988), pp. 43-47.

Laurence, etal., "Erythrocyte CDP-choline accumulation in haemolytic anaemia and renal failure (RF)," Adv. Exp. Med. Biol., 431 (1998), pp. 155-159.

Lew, et al., "Effects of age-dependent membrane transport changes on the homeostasis of senescent human red blood cells", Blood, (Aug. 15, 2007), 110:4, pp. 1334-1342.

Maugh,T.H.,II, "Old blood in surgery is linked to deaths," Chicago Tribune News, (2008), pp. 1-2.

Martin, K., "Active transport of choline into human erythrocytes," J. Physiol, 191 (1967), pp. 105*P-106P*.

Martin, K., "Concentrative accumulation of choline by human erythrocytes," J. Gen Physiol, 51 (1968), pp. 497-516.

Mattingly, P.G., "Chemiluminescent 10-Methyl-Acridinium-9-(N-Sulphonylcarboxamide) Salts. Synthesis and Kinetics of Light Emission", Journal of Bioluminescence and Chemiluminescence, 6 (1991), pp. 107-114.

McCapra, etal., "Chemiluminescence Involving Peroxide Decompositions" 4 (1965), pp. 1111-1121.

McMahon, etal., "Measurement of free choline concentrations in maternal and neonatal blood by micropyrolysis gas chromatography," Clin. Chim. Acta, 149 (1985), pp. 1-12.

Miller, etal., "Factors influencing erythrocyte choline concentrations," Life Sciences, 44 (1989), pp. 477-482.

Miller, etal., "Differences in red blood cell choline and lipid-bound choline between patients with Alzheimer disease and control subjects," Neurobiology of Aging., 12:1 (1991), pp. 61-64.

Molini, etal., "Chemiluminescent Determination of Choline in Cerebrospinal Fluid and Red Blood Cells," J. Biolumin. Chemilumin., 2 (1988), pp. 69-71.

Mudd, etal., "Isolated hypermethioninemia: measurements of S-adenosylmethionine and choline". Metabolsim, 49(2000), pp. 1542-1547.

Nouri-Sorkhabi, etal., "Changes in plasma phospholipids in the presence and absence of erythrocytes $^{31}$P NMR time-course studies," Eur. J. Biochem., 235 (1996), pp. 648-652.

Poli De Figueiredo, etal., "Erythrocyte choline uptake after renal transplantation", The Lancet, 339 (1992), pp. 146-148.

Pomfret, etal., "Measurement of choline and choline metabolite concentrations using high-pressure liquid chromatography and gas chromatography-mass spectrometry". Anal. Biochem., 180 (1989), pp. 85-90.

Razavi, etal., "Stable and versatile active acridinium esters I," Luminescence, 15 (2000), pp. 239-244.

Razavi, etal., "Stable and versatile active acridinium esters II," Luminescence, 15 (2000), pp. 245-249.

Ricciardi, etal., "Porcine hepatic phospholipid efflux during reperfusion after cold ischemia," J.Surg.Res., 103(2002),pp. 79-88.

Riley, etal., "Characterization of human erythrocyte choline transport in chronic renal failure," Nephrology Dialysis Transplantation, 12 (1997), pp. 1921-1927.

Sherman, etal., "Human red blood cell choline uptake with age and Alzheimer's disease," Neurobiology of Aging, 7:3 (1986), pp. 205-209.

Stobbe, M., "Study: Age of Blood May Affect Patients," Chicago Tribune News, (2008), pp. 1-3.

Weltzien, etal., "Cytolytic and membrane-perturbing properties of lysophosphatidylcholine." Biochim Biophys Acta, 559 (1979), pp. 259-287.

Wengelnik, etal., "A Class of Potent Antimalarials and Their Specific Accumulation in Infected Erythrocytes," Science 295, (2002), pp. 1311-1134.

Whalley, etal., "$^{14}$C-Choline Transport into Red Blood Cells in Down's Syndrome," Biol Psychiatry, 14 (1979), pp. 979-982.

Yue, etal., "Choline in Whole Blood and Plasma, Sample Preparation and Stability." Clinical Chemistry, 54:3 (2008) pp. 590-593.

G. C. Leitner, et al., "Quality of Packed Red Blood Cells and Platelet Concentrates Collected by Multicomponent Collection Using the MCS Plus Device", Journal of Clinical Apheresis, Jan. 1, 2003, pp. 21-25 vol. 18, No. 1.

ISA/US, International Search Report and Written Opinion mailed Oct. 22, 2009, International Application PCT/US2009/041182.

* cited by examiner

MEASURING FREE CHOLINE TO DETERMINE SUITABILITY OF ERYTHROCYTES FOR TRANSFUSION

RELATED APPLICATION INFORMATION

None.

TECHNICAL FIELD

The present disclosure relates to a method of assessing the suitability of erythrocytes for transfusion by assessing the level of free choline in the erythrocytes, and a kit for use in such a method. The method and kit can be used to screen potential blood donors and assess the suitability of processed blood products for transfusion prior to use.

BACKGROUND

Every year, about 75 million units of blood are collected worldwide (Klein et al., The Lancet 370: 415-426 (2007)). Units of whole blood (450-500 mL) are collected and refrigerated in plastic packs with an anti-coagulant as a preservative. Whole blood is rarely used for transfusion therapy, however, and its use is limited to massive bleeding, where erythrocytes, also referred to as red blood cells (RBCs), volume, and plasma factors are all needed for survival of the patient. Rather, plasma is removed from whole blood to provide units of RBCs (200-350 mL). Oftentimes, the plasma is replaced with a solution that improves cellular viability during storage.

The transfusion of RBCs is one of the few treatments that adequately restore tissue oxygenation. Depending on the specific indication, RBCs can be filtered, washed, frozen or irradiated.

The safety of blood products used for transfusion-based therapies has always been of great concern. To address those concerns, potential blood donors must first be screened. Initially, the potential donor is required to fill out a questionnaire to assess current and past health, recent medical procedures, recent blood donations, travel to locations with known risk factors and behaviors associated with increased risk. Current examples of such questionnaires are available from AABB—formerly known as the American Association of Blood Banks. Limitations are put on who may donate based on the answers to the questionnaire.

However, data obtained from such questionnaires are subjective in nature and have insufficient reliability to assure the safety of donated blood. Blood donation facilities must, therefore, employ further diagnostic tests that supply objective evidence that the donated blood is safe for use. Such testing may include assays that screen for transmissible infectious agents, such as viruses (e.g., hepatitis B, hepatitis C, human immunodeficiency virus (HIV), human T-lymphotropic virus, cytomegalovirus, and Epstein-Barr virus), parasites (e.g., Chagas, and malaria) and bacteria. The screening of donors and blood products for infectious diseases has dramatically reduced the risk of infection from blood transfusion in developed countries; however, infection remains a major risk in developing countries, where 13 million units of blood are not tested for HIV, hepatitis viruses, and the like (Klein et al. (2007), supra). While pathogen inactivation techniques for RBCs are currently in clinical trials, none is available for use as of yet (Klein et al. (2007), supra).

It is further recognized that donor blood immunologic factors may present a safety hazard for incompatible recipients. So-called "blood group antigens" and so-called "Rh factors" are representative of such immunologic factors, and may lead to hemolytic transfusion reactions.

Additionally, regulatory procedures have been established to define the shelf-life of donated blood and its components. Currently, RBC concentrates in CDPA-1 (citrate, dextrose, phosphate, and adenine) have a shelf-life of 35 days at 1-6° C., while RBCs packed in an additive solution can be stored for 42 days. These limitations are based on the 75% viability of the erythrocytes 24 hours after transfusion. Recent studies have indicated that these criteria may not be sufficient and that poor outcomes may result in patients transfused with RBCs older than 14 days (Koch et al., N. Eng. J. Med. 358: 1229-1239 (2008)). Some researchers have suggested that the increased risk of adverse outcomes is due to depletion of oxygen-carrying chemicals and increased cellular membrane rigidity, among others.

In addition to the above, it is known that more people die from cardiovascular disease than any other disease. Cardiovascular disease accounts for one of every two deaths in the U.S. alone.

Cardiac markers, such as cardiac proteins and cardiac enzymes, are often used in the diagnosis and prognosis of cardiovascular disease. Examples of such markers include troponin, brain natriuretic peptide (BNP), nt-proBNP, creatine kinase isoenzyme MB (CKMB), myoglobin, choline, C-reactive protein (CRP), interleukin-6 (IL-6), tumor necrosis factor $\alpha$ (TNF$\alpha$), placental growth factor (P/GF), pregnancy-associated plasma protein-A (PAPP-A), and soluble CD40 (sCD40). Such markers are measured in the serum or plasma fractions of blood collected from patients displaying one or more clinical symptoms of cardiovascular disease, not in the cellular fraction of blood tested, and more particularly, not in RBCs. Moreover, patients suffering from cardiovascular disease often undergo surgical intervention requiring transfusion of RBCs.

The present inventors have discovered a subpopulation of blood donors that exhibit high levels of free choline in their erythrocytes, while maintaining a normal level of free choline in plasma. Such an elevation of free choline indicates a change in erythrocyte molecular composition, cellular morphology, and biochemistry that constitutes a transmissible factor affecting cardiovascular health.

In view of the foregoing, the present disclosure seeks to provide a method of assessing whether or not erythrocytes are suitable for transfusion. The present disclosure also seeks to provide a kit for use in such a method. The method and kit can be used to screen potential blood donors and assess processed blood products before use in transfusion therapy. These and other objects and advantages, as well as other additional features, will become apparent from the detailed description provided herein.

SUMMARY

A method of assessing whether or not erythrocytes are suitable for transfusion into a recipient in need thereof is provided. The method comprises:

(i) assaying a sample of erythrocytes for free choline, and (ii) comparing the level of free choline in the sample with the level of free choline deemed suitable for use in transfusion therapy. A level of free choline in the sample, which is greater than the level deemed suitable for use in transfusion therapy, indicates that the erythrocytes are not suitable for transfusion. A level of free choline in the sample, which is less than the level deemed suitable for use in transfusion therapy, indicates that the erythrocytes are suitable for transfusion.

Further provided is a kit for use in a method of assessing whether or not the erythrocytes are suitable for transfusion into a recipient in need thereof. The kit comprises at least one reagent for assaying a sample of erythrocytes for free choline. The kit also comprises instructions for conducting the assaying of the sample, and guidelines for assessing the suitability of the erythrocytes for transfusion through the comparison of the level of free choline in the sample with the level of free choline deemed suitable for use in transfusion therapy.

DETAILED DESCRIPTION

Figure 1:
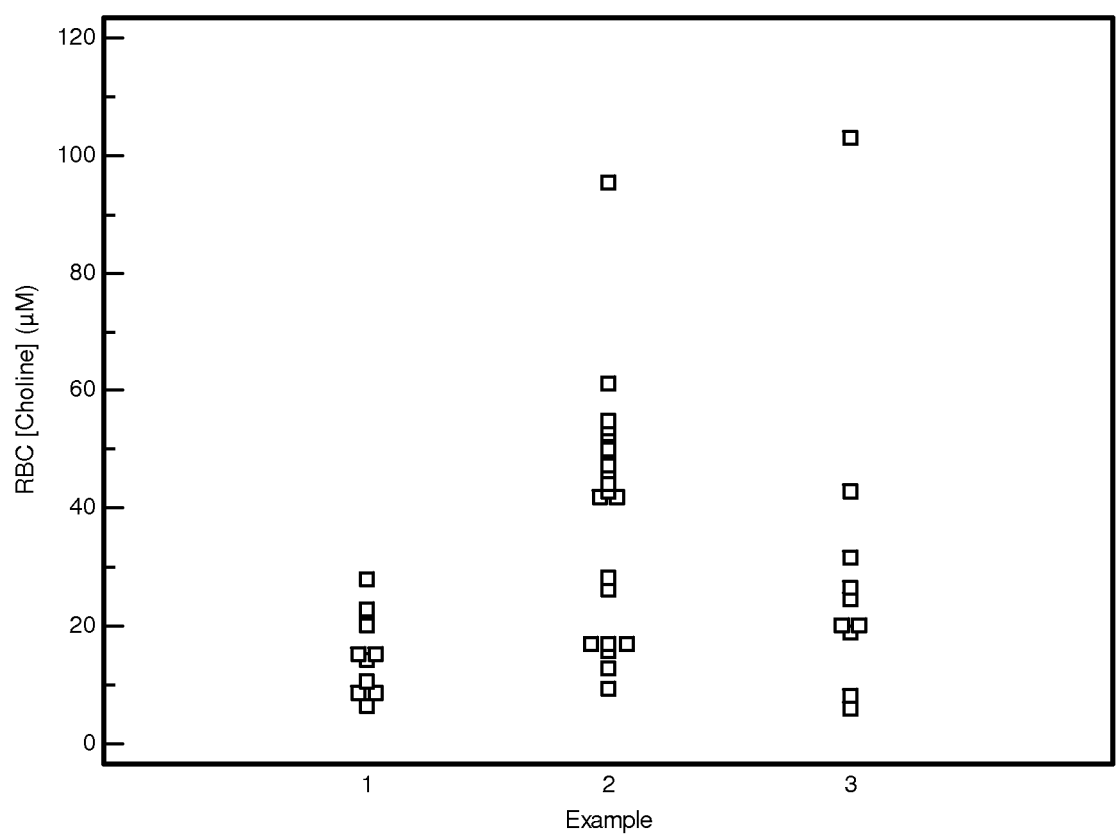
FIG. 1 is a plot of RBC [Choline] (μM) vs. Example (1, 2, and 3).

The present disclosure is predicated, at least in part, on the surprising and unexpected discovery that the free choline content of red blood cells (RBCs) can vary significantly from one source (e.g., donor source, unit of blood, or blood product) to the next, and the choline content in RBCs does not correlate with the level of free choline in plasma or serum from the same source. In view of the foregoing, the present disclosure provides a method of assessing whether or not erythrocytes are suitable for transfusion into a recipient in need thereof. The method comprises (i) assaying a sample of erythrocytes for free choline, and (ii) comparing the level of free choline in the sample with the level of free choline deemed suitable for use in transfusion therapy. By "sample" is meant an aliquot or portion of any medium containing intact erythrocytes, such as that collected by phlebotomy, including venipuncture and capillary puncture, per that art, or that may be obtained from a processed blood product, including packed RBCs, leukocyte-reduced RBCs, washed RBCs, frozen RBCs, and deglycerolized RBCs. The compositions of such processed blood products are known in the art and are described in the literature (e.g., Greer et al. (2003) *Wintrobe's Clinical Hematology*. Lippincott Williams & Wilkins, Philadelphia; Anstee et al. (2005) *Mollison's Blood Transfusion in Clinical Medicine*. 11th ed., Blackwell; and *Blood Banking and Transfusion Medicine: Basic Principles and Practice;* 2nd ed.; Hillyer et al., Eds.; Elsevier/Churchill Livingstone: 2006.) By "erythrocytes" is meant the red blood cell component of whole blood. The erythrocytes may be in substantially non-hemolyzed fresh whole blood. Desirably, the red blood cells are separated substantially from other cellular components of whole blood and plasma. The red blood cells may be processed to reduce further the proportion of whole blood components or prepared for storage per the current art. By "free choline" is meant the compound of the formula:

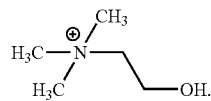

While free choline is structurally represented above in the absence of a counterion, it will be understood by those of ordinary skill in the art that a counterion can be present. It will be further understood that any free choline present in a sample can comprise a mixture of two or more counterions. The presence/absence of a counterion does not materially affect the method of assay or the assessment of the suitability of erythrocytes for transfusion.

By "suitable for use" is meant having a level of free choline below an established upper reference limit. There are many approaches to define an upper reference limit. For example, in the population represented by Example 1 herein, fresh, non-hemolyzed samples containing intact erythrocytes were collected and immediately cooled in ice, then analyzed within 3 hours by the stated chemiluminescent assay. Within that population of healthy normal blood donors, the 90% right-sided reference interval was 24.1 μM. Thus, values below about 24.1 μM of free choline constitute suitability of the erythrocytes for use in transfusion therapies. However, as with other standards, e.g., cholesterol, for which the medically acceptable level continues to trend downward, it is possible that the level of free choline deemed suitable for use may change over time. Thus, the definition of the upper reference limit for normal, suitable erythrocytes may change from about 90% to about 95% or higher (e.g., from about 90% to about 97.5%, or about 90%, about 91%, about 92%, about 93%, about 94%, about 95%, about 96%, or about 97%). It is intended that the level accepted in the art at the time of assay be used. In this regard, other factors, such as the current availability of erythrocytes from a particular blood group, the existence of a natural or man-made disaster, and the like, may be taken into consideration when determining the suitability of erythrocytes for transfusion by comparing the level of free choline in the sample with the medically acceptable standard at the time of assaying. For example, rather than ruling out samples having a level of free choline greater than or equal to about 24.1 μmol/L for transfusion, some leeway may be tolerated under such circumstances. Perhaps, samples having a level of free choline as high as about 30 μmol/L, for example, may be deemed suitable under such circumstances. Desirably, potential donors having a level of free choline greater than about 24.1 μmol/L+about 5.0% are excluded. Further, it is recognized that the upper reference limit of free choline defining "suitable for use" may change depending on the method of analysis or laboratory and, thus, must be determined for each method and laboratory using a well-defined normal population and comparison to standards and other validated methods. Thus, explicitly recognized herein is the value of assessing and monitoring the free choline content of erythrocytes, in particular in determining the suitability of erythrocytes for use in transfusion and in screening potential donors for erythrocytes suitable for transfusion.

Any suitable method as known in the art can be used to assay for the level of free choline. The method can be direct or indirect, homogeneous or heterogeneous, competitive or non-competitive, and can involve liquid and/or solid phases. Chromatography, including high pressure liquid chromatography and gas chromatography, mass spectrometry, immunoassay (e.g., affinity chromatography, immuno-electrophoresis, radioimmunoassay, enzyme-linked immunosorbent assay, Western blot, and the like), microparticle separation, and/or precipitation techniques can be employed, among others. The means of detection can involve the use of chemiluminescence (e.g., acridinium labels, such as described herein, luminol, isoluminol, phenanthridinium esters, and the like), bioluminescence, fluorescence (e.g., fluorescein), magnetic labels, enzymatic labels (e.g., horseradish peroxidase, alkaline peroxidase, glucose 6-phosphate dehydrogenase, and the like), rhodamine, phycobiliproteins, R-phycoerythrin, quantum dots (e.g., zinc sulfide-capped cadmium selenide), thermometric labels, immunopolymerase chain reaction labels, and radioactivity, among others. An introduction to labels, labeling procedures, and detection of labels is found in Polak and Van Noorden, *Introduction to Immunocytochemisty*, 2$^{nd}$ ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. Preferably, the method enables the simultaneous assay of a large number of samples of small volume. In one embodiment, a chemiluminescent assay, such as a homogeneous chemiluminescent assay, is preferred.

A suitable homogeneous chemiluminescent assay comprises (i) contacting the sample with choline oxidase, which converts free choline to betaine and results in the production of a peroxide, and (ii) reacting the peroxide with (a) an acridinium-9-carboxamide in the presence of a base or (b) an acridinium-9-carboxylate aryl ester in the absence of protein and in the presence of a base, whereupon acridone and a light signal, which is proportional to the amount of free choline in the sample, are generated.

In general, the present disclosure relates to an assay for free choline in a sample of erythrocytes. The sample can be obtained from any vertebrate, preferably a mammal, such as a human, primate, horse, pig, cow, sheep, goat, rat, mice, rabbit, cat or dog. The sample can be obtained using routine techniques known to those skilled in the art. The sample of erythrocytes can be pretreated to modify the character of the sample. Such pretreatment can involve filtration, precipitation, dilution, mixing, concentration, inactivation of interfering components, the addition of reagents, lysing, freezing, heating, etc. Specifically, as will be described in more detail below, the processing of the sample containing free choline to separate or remove protein contained in the sample or to separate or remove free choline from the sample (and thus away from protein contained in the sample) allows for the use of one or more acridinium aryl esters of a particular formula described herein in the quantification of the amount of free choline contained in the sample.

When choline oxidase is added to the sample, such as in an amount from about 0.0001 units/mL to about 10,000 units/mL, free choline is oxidized to betaine, and hydrogen peroxide is produced. Hydrogen peroxide reacts with an acridinium-9-carboxamide or acridinium-9-carboxylate aryl ester, producing a light signal, which is proportional to the amount of free choline in the sample.

While any suitable acridinium compound can be used in the context of the methods disclosed herein, preferably the acridinium is an acridinium-9-carboxamide or an acridinium-9-carboxylate aryl ester. Preferably, the acridinium-9-carboxamide is an acridinium-9-carboxamide of formula I:

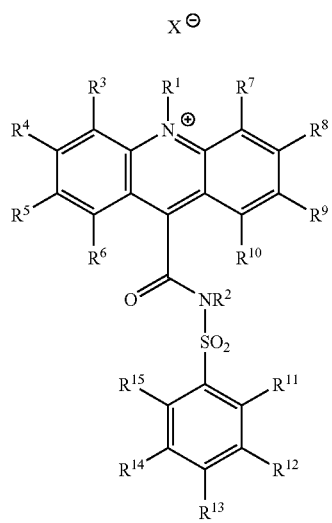

I wherein $R^1$ and $R^2$ are each independently selected from the group consisting of: alkyl, alkenyl, alkynyl, aralkyl, aryl, sulfoalkyl, carboxyalkyl and oxoalkyl, and wherein $R^3$ through $R^{15}$ are each independently selected from the group consisting of: hydrogen, alkyl, alkenyl, alkynyl, aryl, aralkyl, amino, amido, acyl, alkoxyl, hydroxyl, carboxyl, halogen, halide, nitro, cyano, sulfo, sulfoalkyl, carboxyalkyl and oxoalkyl; and if present, $x^\ominus$ is an anion.

Preferably, the acridinium ester is an acridinium-9-carboxylate aryl ester of formula II:

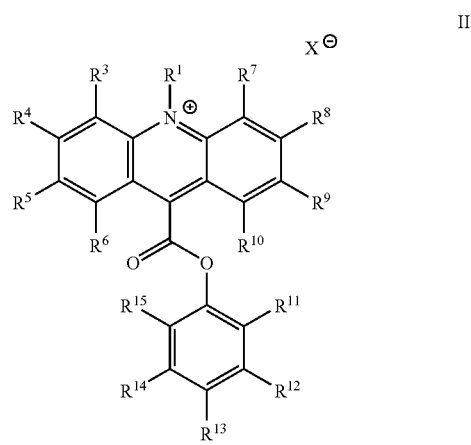

II wherein $R^1$ is an alkyl, alkenyl, alkynyl, aryl, aralkyl, sulfoalkyl, carboxyalkyl, or oxoalkyl; and wherein $R^3$ through $R^{15}$ are each independently selected from the group consisting of: hydrogen, alkyl, alkenyl, alkynyl, aryl, aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Acridinium-9-carboxylate aryl esters of the above formulae are readily (commercially) available. A non-limiting example of a commercially available acridinium-9-carboxylate aryl ester, which is useful in the context of the disclosed methods and kits, is 10-methyl-9-(phenoxycarbonyl)acridinium fluorosulfonate (available from Cayman Chemical, Ann Arbor, Mich.).

With respect to the above formulae, "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

"Alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

"Alkynyl" means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

"Aryalkyl" means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

"Aryl" means a phenyl group, or a bicyclic or tricyclic fused ring system in which one or more of the fused rings is a phenyl group. Bicyclic fused ring systems are exemplified by a phenyl group fused to a cycloalkenyl group, as defined herein, a cycloalkyl group, as defined herein, or another phenyl group. Tricyclic fused ring systems are exemplified by a bicyclic fused ring system fused to a cycloalkenyl group, as defined herein, a cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkoxy, alkyl, carboxyl, halo, and hydroxyl.

"Cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

"Cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present invention can be optionally substituted with one, two, three, four, or five substituents independently selected from the group consisting of alkoxy, alkyl, carboxyl, halo, and hydroxyl.

"Sulfoalkyl" refers to an alkyl group to which a sulfonate group is bonded, wherein the alkyl is bonded to the molecule of interest, whereas "carboxyalkyl" refers to an alkyl group that is substituted with one or more carboxy groups, "oxoalkyl" refers to an alkyl group that is substituted with one or more oxy groups, "amino" means $-NR_aR_b$, wherein $R_a$ and $R_b$ are independently selected from the group consisting of hydrogen, alkyl and alkylcarbonyl, "amido" means $-C(O)NR_aR_b$, wherein $R_a$ and $R_b$ are independently selected from the group consisting of hydrogen and alkyl, "acyl" means RC(O)—, "alkylcarbonyl," means an alkyl group attached to the parent molecular moiety through a carbonyl group, "alkoxy" or "alkoxyl" means an alkyl group, as defined herein, appended to the parent molecular moiety through an oxygen atom, representative examples of which include, but are not limited to, methoxy, ethoxy, propoxy, 2-propoxy, butoxy, tert-butoxy, pentyloxy, and hexyloxy, "hydroxyl" means an —OH group, "carboxy" or "carboxyl" refers to —CO$_2$H, "halogen" means —Cl, —Br, —I or —F, "halide" means a binary compound, of which one part is a halogen atom and the other part is an element or radical that is less electronegative than the halogen, e.g., an alkyl radical, "nitro" means a —NO$_2$ group, "sulfo" means SO$_3$H, and "cyano" means a —CN group.

"Anion" refers to an anion of an inorganic or organic acid. Examples include, but are not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid, fluorosulfonic acid, and any combinations thereof.

Methods for preparing acridinium 9-carboxamide are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*. Dyke, Ed., CRC Press: Boca Raton, pp. 77-105 (2002); Adamczyk et al., Org. Lett. 5: 3779-3782 (2003); and U.S. Pat. Nos. 5,468,646; 5,543,524; and 5,783,699, each of which is specifically incorporated herein by reference in its entirety for its teachings regarding same.

Methods for preparing acridinium 9-carboxylate aryl esters are described in McCapra et al., Photochem. Photobiol. 4: 1111-1121 (1965); Razavi et al., Luminescence 15: 245-249 (2000a); Razavi et al., Luminescence 15: 239-244 (2000b); and U.S. Pat. No. 5,241,070. Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90% and about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

Chemiluminescent assays for free choline can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed. For example, the emission of light from an acridinium carboxamide can be a pseudo-flash when the reagents are added in rapid succession, such as within 5 seconds, whereas the emission of light from an acridinium carboxamide can be a long-lived glow when there is a delay, such as 20 seconds, between the addition of choline oxidase and the acridinium carboxamide.

Upon the addition of the acridinium, e.g., acridinium-9-carboxamide or acridinium-9-carboxylate aryl ester, and the simultaneous or subsequent addition of at least one basic solution to the sample, a detectable signal, namely, a chemiluminescent signal, indicative of the presence of free choline is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of free choline in the sample can be quantified. Specifically, the amount of free choline in the sample is proportional to the intensity of the signal generated. The amount of free choline present can be quantified by comparing the amount of light generated to a standard curve for free choline or by comparison to a reference standard. The standard curve can be generated using serial dilutions or solutions of known concentrations of free choline by mass spectroscopy, gravimetric methods, and other techniques known in the art.

In view of the above, the present disclosure also provides a kit. The kit can be used in a method of assessing whether or not erythrocytes are suitable for transfusion into a recipient in need thereof. The kit comprises at least one reagent for assaying a sample of erythrocytes for free choline, instructions for conducting the assaying of the sample, and guidelines for assessing the suitability of the erythrocytes for transfusion through the comparison of the level of free choline in the sample with the level of free choline deemed suitable for transfusion. The instructions can comprise instructions for detecting free choline in the sample, instructions for generating a standard curve for the purpose of quantifying free choline in the sample or a reference standard, and the like. If the kit includes acridinium-9-carboxylate aryl ester, the instructions will describe the steps necessary to render the sample sufficiently free from protein such that a detectable chemiluminescent signal can be generated. Alternatively, the instructions will refer to a publication or well-known textbook that describes protocols for performing ultrafiltration, extraction, precipitation, dialysis, chromatography, digestion, and the like. The kit can comprise one or more of the following reagents: (i) choline oxidase, (ii) at least one acridinium-9-carboxamide and/or at least one acridinium-9-carboxylate aryl ester, and (iii) at least one basic solution/buffer.

The following examples are provided for purposes of illustration. The examples are not intended to limit the scope of the appended claims.

Example 1

This example describes the analysis of samples of lysed whole blood, plasma, and erythrocytes for free choline.

Ten random samples of whole blood were collected in ethylene diamine tetra-acetic acid (EDTA), kept on ice, and analyzed within three hours of drawing. Microhematocrits were measured for each sample using Clay Adams™ SurePrep™ precalibrated capillary microhematocrit tubes and a Triac centrifuge (Becton, Dickinson & Co., Franklin Lakes, N.J.).

Whole blood samples were gently inverted for 10 cycles to resuspend RBCs from the bottoms of the tubes. An aliquot of each sample of whole blood (0.5 mL) was added to separate 1.5 mL microfuge tubes. The tubes were spun in a Beckman centrifuge at 5° C. for 20 min at 2,000 g. Plasma was removed from each tube and placed in a separate microfuge tube for testing. The tubes of plasma were stored at 2-8° C. until testing. RBCs were resuspended in heat-inactivated (58° C., 3 hours), phosphate-buffered saline containing 0.5% human serum albumin (1 mL) by gentle mixing. The samples of RBCs were then centrifuged as above. The cells were washed twice, after which the pelleted cells (100 μl) were removed and reconstituted in a separate tube with distilled water (200 μl).

RBCs were lysed with a quick freeze/thaw protocol consisting of three freeze-thaw cycles of immersion in liquid nitrogen alternating with immersion in nearly boiling water within a 15-minute period. Whole blood samples were lysed by the same freeze-thaw cycle.

Free choline levels were determined using the chemiluminescent microplate assay of Adamczyk et al. ((2006), supra) using 10K MW microfuge filters for the lysed whole blood and RBC sample types. Plasma samples were analyzed neat.

Example 2

This example describes the analysis of samples of lysed whole blood, plasma, and erythrocytes for free choline.

Twenty random samples of whole blood were collected in EDTA, kept on ice, and analyzed within 24 hours of drawing. The samples were analyzed for free choline according to the procedures of Example 1.

Example 3

This example describes the analysis of samples of lysed whole blood, plasma, and erythrocytes for free choline.

Ten random samples of whole blood in CDP (citrate, dextrose, and phosphate) were collected, maintained at 2-8° C., and analyzed within 24 hours of drawing. The samples were analyzed for free choline according to the procedures of Example 1.

Figure 2:
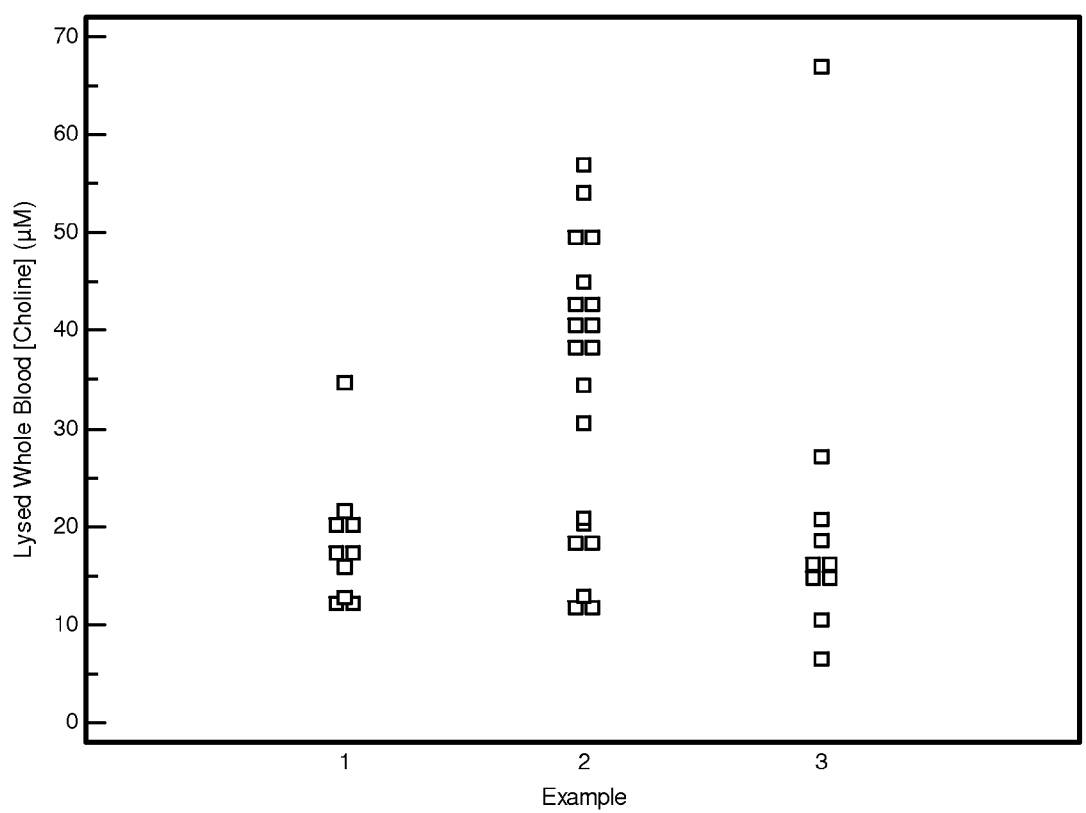
FIG. 2 is a plot of lysed whole blood [Choline] (μM) vs. Example (1, 2, and 3).
Figure 3:
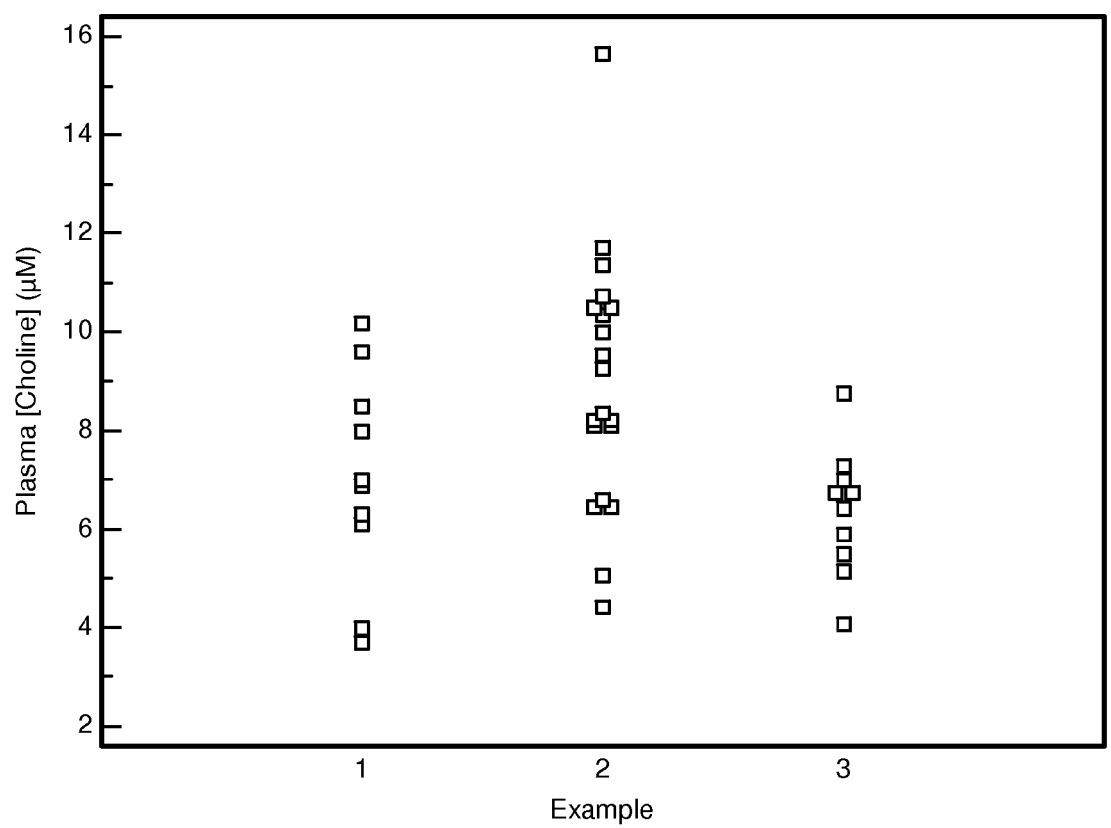
FIG. 3 is a plot of plasma [Choline] (μM) vs. Example (1, 2, and 3).

With respect to the above examples, the concentration of free choline in RBCs (see FIG. 1) ranged from 6.66 μM to 28.17 μM, with an average of 15.30 μM, for the 3-hour samples, 6.93 μM to 81.99 μM, with an average of 36.02 μM, for the 24-hour samples in EDTA, and 6.00 μM to 103.05 μM, with an average of 30.34 μM, for the 24-hour samples in CDP. The concentration of free choline in lysed whole blood (see FIG. 2) ranged from 12.31 μM to 34.82 μM, with an average of 18.57 μM, for the 3-hour samples, 11.89 μM to 57.06 μM, with an average of 34.03 μM, for the 24-hour samples in EDTA, and 6.49 μM to 67.06 μM, with an average of 21.37 μM, for the 24-hour samples in CDP. The concentration of free choline in plasma (see FIG. 3) ranged from 3.70 μM to 10.2 μM, with an average of 7.03 μM, for the 3-hour samples, 4.42 μM to 15.64 μM, with an average of 8.99 μM, for the 24-hour samples in EDTA, and 4.08 μM to 8.77 μM, with an average of 6.37 μM, for the 24-hour samples in CDP. Thus, the range of free choline concentration and the average free choline concentration in RBCs (see FIG. 1) and whole blood (see FIG. 2) were higher for samples collected in EDTA and analyzed after 24 hours compared to samples collected in EDTA and analyzed within 3 hours. The concentration of free choline in erythrocytes collected in CDP, a common anticoagulant used in processed blood products for transfusion therapy, and analyzed within 24 hours (Example 3), was also significantly higher on average than in erythrocytes collected in EDTA and analyzed within 3 hours of collection. There was no correlation between plasma and RBC free choline concentrations, and poor correlation between plasma and lysed whole blood free choline concentrations. In contrast, there was good correlation between lysed whole blood and RBC free choline concentrations. In addition, the theoretical summation of plasma free choline and RBC free choline (hematocrit adjusted) correlated well with lysed whole blood free choline. The examples demonstrate that RBCs contain free choline, the free choline content of RBCs can vary significantly from one source to the next, and the free choline content of RBCs can increase over time.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods, and/or steps of the type described herein and/or which will become apparent to those ordinarily skilled in the art upon reading the disclosure. The terms and expressions, which have been employed, are used as terms of description and not of limitation. There is no intention in the use of such terms and expressions of excluding any equivalents of the features shown and described or portions thereof. It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of assessing whether or not erythrocytes are suitable for transfusion into a recipient in need thereof, which method comprises:
   (i) assaying a sample of erythrocytes for free choline, and
   (ii) comparing the level of free choline in the sample with the level of free choline deemed suitable for transfusion therapy;
   wherein a level of free choline in the sample, which is greater than a predetermined upper reference limit, indicates that the erythrocytes are not suitable for transfusion,
   whereas a level of free choline in the sample, which is less than the predetermined upper reference limit, indicates that the erythrocytes are suitable for transfusion,
   whereupon the erythrocytes are assessed for suitability for transfusion.

2. The method of claim 1, wherein (i) is performed using a chemiluminescent assay.

3. The method of claim 2, wherein the chemiluminescent assay comprises (i) contacting the sample with choline oxidase, which converts free choline to betaine and results in the production of a peroxide, and (ii) reacting the peroxide with (a) an acridinium-9-carboxamide in the presence of a base or (b) an acridinium-9-carboxylate aryl ester in the absence of protein and in the presence of a base, whereupon acridone and a light signal, which is proportional to the amount of free choline in the sample, are generated.

\* \* \* \* \*